United States Patent [19]
Hendi

[11] Patent Number: 5,840,907
[45] Date of Patent: Nov. 24, 1998

[54] PROCESS FOR PREPARING DIKETOPYRROLOPYRROLE DERIVATIVES

[75] Inventor: Shivakumar Basalingappa Hendi, Newark, Del.

[73] Assignee: Ciba Specialty Chemicals Corporation, Tarrytown, N.Y.

[21] Appl. No.: 870,353

[22] Filed: Jun. 5, 1997

Related U.S. Application Data

[60] Provisional application No. 60/019,138 Jun. 5, 1996.

[51] Int. Cl.$^6$ .................. C07D 487/04; C07D 519/00
[52] U.S. Cl. ............................ 546/256; 548/453
[58] Field of Search ............... 546/256; 548/453

[56] References Cited

U.S. PATENT DOCUMENTS

| | | | |
|---|---|---|---|
| 4,585,878 | 4/1986 | Jost et al. | 548/453 |
| 4,791,204 | 12/1988 | Jost et al. | 548/101 |
| 4,931,566 | 6/1990 | Surber et al. | 548/453 |
| 5,646,299 | 7/1997 | Hao et al. | 548/453 |

*Primary Examiner*—Joseph K. McKane
*Attorney, Agent, or Firm*—Kevin T. Mansfield

[57] ABSTRACT

This disclosure relates to a process for preparing bis (hydroxymethyl)pyrrolopyrrole compounds of the formula

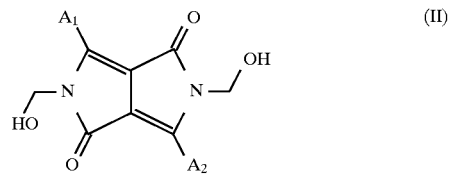

(II)

wherein $A_1$ and $A_2$ are aryl radicals, by reacting a 1,4-diketopyrrolopyrrole with formaldehyde. The compound of formula (II) can be isolated or further reacted in a one pot synthesis to yield a compound of the formula

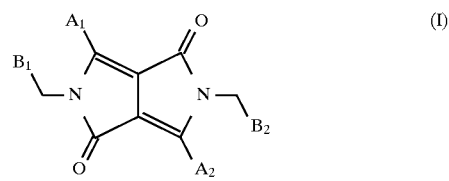

(I)

wherein $B_1$ and $B_2$ are organic radicals.

9 Claims, No Drawings

5,840,907

PROCESS FOR PREPARING DIKETOPYRROLOPYRROLE DERIVATIVES

This application claims the benefit under 35 USC 119(e) of U.S. Provisional application Ser. No. 60/019,138, filed on Jun. 5, 1996.

SUMMARY

This application relates to a process for preparing 1,4-diketo-3,6-diarylpyrrolopyrrole derivatives wherein a diketopyrrolopyrrole is reacted with formaldehyde to yield a 2,5-bis(hydroxymethyl)-3,6-diarylpyrrolopyrrole-1,4-dione which is isolated or further reacted.

BACKGROUND

Diaryldiketopyrrolopyrroles of the formula

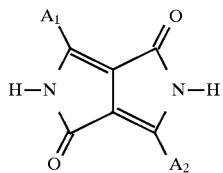

wherein $A_1$ and $A_2$ are aryl radicals are well-known as important pigments.

U.S. Pat. No. 4,585,878 discloses N-substituted derivatives of the diaryldiketopyrrolopyrrole pigments wherein the N-substituent does not confer solubility in water. According to U.S. Pat. No. 4,585,878, the N-substituted derivatives of the diaryldiketopyrrolopyrrole pigments are prepared by reacting a diaryldiketopyrrolopyrrole compound in an organic solvent with a compound containing the ultimate N-substituents attached to a leaving group, or by reacting 2 moles of a compound of the formula R—N=CH—A, wherein R is the N-substituent and A is an aryl group, or one mole each of two different compounds of the formula R—N=CH—A, with a succinic acid diester in the presence of a base and an organic solvent and then dehydrogenating the product.

The present invention relates to a process for preparing a variety of N-substituted derivatives of diaryldiketopyrrolopyrrole pigments wherein the N-substituents are linked to the diaryldiketopyrrolopyrrole by —$CH_2$— or —O—$CH_2$— linkages. The inventive process involves reacting a diaryldiketopyrrolopyrrole with formaldehyde to yield a 2,5-bis(hydroxymethyl)-3,6-diarylpyrrolopyrrole-1,4-dione intermediate and further reacting the intermediate, with or without isolation, with a second reactant which reacts with the hydroxymethyl groups. The products of the reaction are useful as colorants and as rheology improving agents for pigment dispersions. The 2,5-bis(hydroxymethyl)-3,6-diarylpyrrolopyrrole-1,4-dione intermediate is a useful as a synthon for the preparation of a variety of DPP derivatives, and as a stabilizer for polymers.

DETAILED DESCRIPTION

The present invention relates to a process of preparing a diketopyrrolopyrrole derivative of the formula (I)

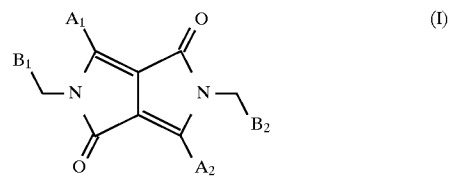

wherein $A_1$ and $A_2$ are identical or different aryl radicals and $B_1$ and $B_2$ are identical or different organic radicals; which diketopyrrolopyrrole derivative contains from 0 to 6 moles of —$SO_3M$ per mole of the diketopyrrolopyrrole derivative; wherein M is hydrogen or a metal or ammonium cation, which process comprises a reaction wherein a 1,4-diketo-3,6-diarylpyrrolo[3,4-c]pyrrole of the formula

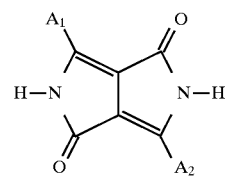

is reacted in a first step with formaldehyde to yield a sulfonated or non-sulfonated intermediate of the formula

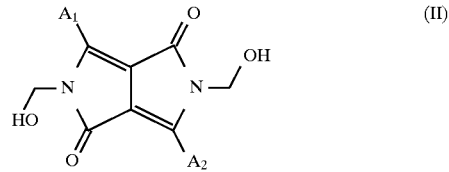

which intermediate reacts in a second step with a precursor of the organic radicals, $B_1$ and $B_2$, to yield the diketopyrrolopyrrole derivative of formula (I). In general, the second reactant reacts with the compound of formula (II) by a substitution reaction or to form an —O— linkage.

The first step is preferably carried out by adding the 1,4-diketo-3,6-diarylpyrrolo[3,4-c]pyrrole to a solution of paraformaldehyde in concentrated sulfuric acid, preferably having a $H_2SO_4$ concentration greater than 90 percent by weight, most preferably above 95 percent by weight.

In general, the stoichiometric amount of formaldehyde is used in the first step. Thus, the molar ratio of the 1,4-diketo-3,6-diarylpyrrolo[3,4-c]pyrrole to the formaldehyde during the first step is preferably 1:2.

After step (a) is complete, the resulting intermediate is reacted with the precursor to yield the diketopyrrolopyrrole derivative of formula (I).

Preferably, both steps are carried out at a temperature of from 20° to 100° C. If a high degree of sulfonation is desired, the process is carried out at higher temperatures, for example above 40° C. If it is desirable to have a low degree of sulfonation, the reaction is maintained at a lower temperature, preferably 40° C. or below.

After the reaction is complete, the 1,4-diketo-3,6-diarylpyrrolo[3,4-c]pyrrole derivative is isolated by procedures conventionally used in the art for isolating 1,4-diketo-3,6-diarylpyrrolo[3,4-c]pyrroles, in particular by pouring the sulfuric acid solution into ice water maintaining the temperature below 10° C. and stirring the resulting aqueous slurry for about 1 hour, followed by filtration, washing and drying to yield the 1,4-diketo-3,6-diarylpyrrolo[3,4-c] pyrrole derivative in solid form.

Since it is not necessary to isolate the intermediate, the inventive process is preferably a one pot process. However, it is possible to isolate the intermediate prior to carrying out the second step, especially, for example, in those instances where it is desired to carry out the second step in a solvent other than the solvent used for the first step.

Suitable solvents for the second step include concentrated sulfuric acid, polyphosphoric acid and organic solvents which do not react with the compound of formula (II), especially polar organic solvents such as acetonitrile, benzonitrile, dimethylformamide, dimethylsulfoxide, tetramethylenesulfone.

It is also possible to carry out the second step in a solvent which reacts with the compound of formula (II) to yield the desired product, for example, $C_1$–$C_{10}$ alcohols are suitable solvents if the compound of formula (I) is the ether obtainable by reacting the compound of formula (II) with the alcohol.

Preferably, the diketopyrrolopyrrole derivatives of formula (I) contain from 0 to 4 moles of —$SO_3M$ per mole of diketopyrrolopyrrole derivative; most preferably from 0 to 2 moles per mole of diketopyrrolopyrrole derivative. In general, if the reaction is carried out at about 40°–50° C., the product contains about 0.5 moles of —$SO_3M$ per mole of diketopyrrolopyrrole derivative.

M is preferably hydrogen, or an alkali metal, such as sodium or potassium, an alkaline earth metal, such as magnesium, an aluminum, a zinc or an ammonium cation. Examples of suitable ammonium cations include quaternary ammonium cations, such as trimethylcetylammonium or tributylbenzylammonium.

$A_1$ and $A_2$ as aryl include both aromatic and heteroaromatic radicals. Radicals which are particularly suitable as $A_1$ and $A_2$ include radicals of the formula

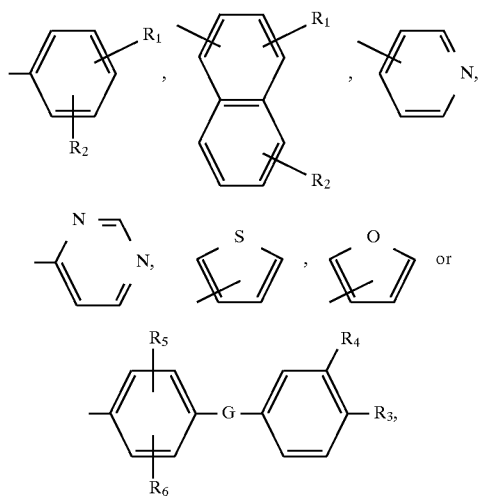

wherein $R_1$ and $R_2$ are each independently of the other hydrogen, halogen, $C_1$–$C_{18}$alkyl, $C_1$–$C_{18}$alkoxy, $C_1$–$C_{18}$alkylmercapto, $C_1$–$C_{18}$alkylamino, $C_1$–$C_{18}$alkoxycarbonyl, $C_1$–$C_{18}$alkylaminocarbonyl, —CN, —$NO_2$, trifluoromethyl, $C_5$–$C_6$cycloalkyl, —C=N—($C_1$–$C_{18}$alkyl), phenyl,

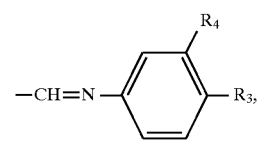

imidazolyl, pyrrazolyl, triazolyl, piperazinyl, pyrrolyl, oxazolyl, benzoxazolyl, benzothiazolyl, benzimidazolyl, morpholinyl, piperidinyl or pyrrolidinyl, G is —$CH_2$—, —$CH(CH_3)$—, —$C(CH_3)_2$—, —CH=N—, —N=N—, —O—, —S—, —SO—, —$SO_2$—, —CONH— or —$NR_7$—, $R_3$ and $R_4$ are each independently of the other hydrogen, halogen, $C_1$–$C_6$alkyl, $C_1$–$C_{18}$alkoxy or —CN, $R_5$ and $R_6$ are each independently of the other hydrogen, halogen or $C_1$–$C_6$alkyl, and $R_7$ is hydrogen or $C_1$–$C_6$alkyl.

In particular, $A_1$ and $A_2$ are each a group of formula

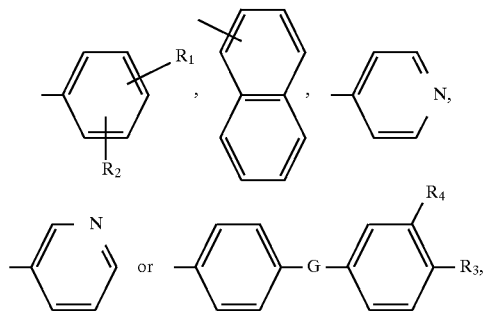

wherein $R_1$ and $R_2$ are each independently of the other hydrogen, chloro, bromo, $C_1$–$C_4$alkyl, $C_1$–$C_6$alkoxy, $C_1$–$C_6$alkylamino, phenyl or CN, G is —O—, —$NR_7$—, —N=N— or —$SO_2$—, $R_3$ and $R_4$ are hydrogen, and $R_7$ is hydrogen, methyl or ethyl, and more particularly $A_1$ and $A_2$ are each a group of formula

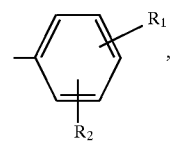

wherein $R_1$ and $R_2$ are each independently of the other hydrogen, methyl, tert-butyl, chloro, bromo, phenyl or CN. At least one of $R_1$ and $R_2$ is preferably hydrogen. Most preferably, at least one of $R_1$ and $R_2$ is hydrogen and the other is in the 4 position of the phenyl ring.

The organic radicals $B_1$ and $B_2$ are derivable from a precursor which reacts with the hydroxy groups of a compound of the formula (II) either by a substitution reaction or to form an —O— linkage.

Precursors which react with a hydroxyl group by a substitution reaction are generally compounds which comprise an aromatic radical, a heteroaromatic radical, or radicals of the formulae X—C(=O)—Y—, X—C(=O)—Y—, —Y—C(=O)—O—X, X—C(=S)—Y—, —Y—C(=S)—O—X, —Y—C(=S)—S—X, X—C(=N)—Y—, XZN—, X—S—, X—$SO_2$—, X—$SO_2$—$NR_{10}$—,

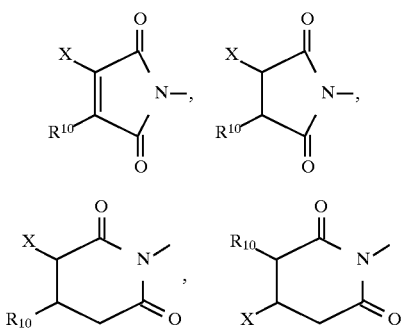

and —N(R$_{10}$)—C(=O)—O—X; wherein X and Z are each hydrogen or an aliphatic, alicyclic, araliphatic, aromatic or heterocyclic radical, or X and Z together form a 3 to 8 membered ring, Y is the residue of an active methylene containing moiety, and R$_{10}$ is hydrogen, an aliphatic radical, an alicyclic radical, an araliphatic radical, an aromatic radical or a heterocyclic radical, or R$_{10}$ and X together form a 3 to 8 membered ring.

Examples of B$_1$ and B$_2$ radicals derivable from a precursor which reacts with a hydroxyl group to form an —O— linkage include an alkyl halide and radicals of the formulae X—C(=O)O—, X—C(=S)O—, X—SO$_2$—O—, XO—; wherein X has the meaning given above.

As aromatic radicals, B$_1$ and B$_2$ especially include radicals containing 1, 2, 3, 4 or more phenyl rings which are bonded directly to each other, bonded to each other through a linking group, fused, or any combination thereof. The biphenylyl radical is an example of two phenyl rings directly bonded to each other. Radicals of the formulae

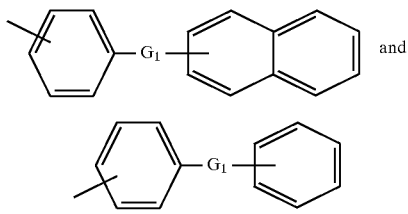

wherein G$_1$ is a linking group, are examples of phenyl rings bonded through each other through a linking group. Examples of aromatic radicals containing fused phenyl rings include naphthyl, anthryl and phenanthryl.

The linking group G$_1$ is especially those linking groups described above for the variable G.

As heteroaromatic radicals, B$_1$ and B$_2$ especially include radicals containing one or more 5, 6 or 7 membered aromatic rings containing from 1 to 4 heteroatoms. In general, the heteroatom(s) are nitrogen, oxygen, sulfur or any combination thereof. Suitable heteroaromatic radicals include the pyrrolopyrroles, especially the 1,4-diketo-3,6-diarylpyrrolo [3,4-c]pyrroles and quinacridones.

Y is the residue of an active methylene containing moiety. Active methylene moieties are generally those methylene groups which are linked to an electron withdrawing substituent, such as a carbonyl or nitrile substituent. In general, active methylene moieties participate in a Mannich type or similar reaction. In general, Y is —CHX, —CH$_2$—X or —(CH=CH)$_n$—CH$_2$—X, wherein n is 1, 2 or 3. When Y is the —CHX— radical, the —CHX— radical is part of a ring, for example, when B$_1$ or B$_2$ is the X—C(=O)—Y— radical, X and Y can form part of, for example, a cyclohexanone ring.

X and Z are aliphatic, alicyclic, araliphatic, aromatic or heterocyclic radicals.

In general, aliphatic radicals include C$_1$–C$_{10}$ alkyl, C$_1$–C$_{10}$ alkenyl, and C$_1$–C$_{10}$ alkynyl radicals, including straight and branched chains.

Alicyclic radicals include those moieties containing only one or more nonaromatic hydrocarbon rings. Important alicyclic radicals include radicals derived from C$_3$–C$_8$-cycloalkanes and C$_3$–C$_8$cycloalkenes. Examples of important alicyclic radicals include cyclopentyl, cyclohexyl and cycloheptyl. Alicyclic radicals also include those moieties wherein there is, for example, a —C(=O)— on the ring, such as cyclohexanone.

Araliphatic radicals are those moieties which contain an aliphatic portion and an aromatic portion, for example a phenyl or heteroaromatic portion. Examples of araliphatic radicals include radicals derived from the phenylalkanoic acids, the naphthylalkanoic acids, the pyridine alkanoic acids, the quinoline alkanoic acids, the indole alkanoic acids, such as those derived from phenyl acetic acid, phenyl propionic acid, or indole acetic acid.

Aromatic radicals suitable as X and Z include those described above as being useful as B$_1$ and B$_2$. The term "aromatic" radical, in this instance, does not include heteroaromatic radicals.

Heterocyclic radicals contain one or more nonaromatic and/or aromatic rings which contain one or more heteroatoms; especially 3 to 8 membered rings which contain 1 to 3 heteroatoms, which heteroatoms are especially nitrogen, sulfur and oxygen. The term heterocyclic radical includes fused ring systems wherein one or more rings contain one or more heteroatoms. Important heterocyclic radicals include pyridinyl, pyranyl, tetrahydrofuranyl, morpholino, pyrimidyl, pyrone, oxazine, azepinyl, triazinyl, oxathiazinyl, pyrroyl, benzofuranyl, piperazinyl, oxathiazolyl, oxadiazolyl, quinolinyl, indolyl, carbazolyl, xanthenyl, acridinyl, coumarinyl, benzoxazolyl, benzopyrone, quinazolinyl. Heterocyclic radicals include those wherein the ring is a lactone or a lactam.

The description of radicals above also defines aliphatic, alicyclic, araliphatic, aromatic and heterocyclic radicals suitable as R$_{10}$. When R$_{10}$ combines with X to form a ring, the ring is preferably a five or six membered ring.

The aromatic, heterocyclic, aliphatic, alicyclic and araliphatic radicals are unsubstituted (by any group other than hydrogen) or substituted by one or more, preferably 0 to 4, customary substituents.

Customary substituents include hydroxy, carbonyl, halogen, C$_1$–C$_{18}$alkyl, C$_1$–C$_{18}$alkoxy, C$_1$–C$_{18}$alkylmercapto, C$_1$–C$_{18}$alkylamino, di(C$_1$–C$_{18}$alkyl) amino, C$_1$–C$_{18}$alkoxycarbonyl, C$_1$–C$_{18}$alkylaminocarbonyl, —CN, —NO$_2$, trifluoromethyl, C$_5$–C$_6$cycloalkyl, —C=N—(C$_1$–C$_{18}$-alkyl) and phenyl, wherein the alkyl groups can be further substituted by hydroxyl, halogen, nitro, C$_1$–C$_6$alkoxy, carbonyl, —CN.

Substituents defined as halogen are typically iodo, fluoro, bromo and, preferably, chloro;

C$_1$–C$_6$alkyl is typically methyl, ethyl, n-propyl, isopropyl, n-butyl, sec-butyl, tert-butyl, n-amyl, tert-amyl, hexyl, and C$_1$–C$_{10}$alkyl and C$_1$–C$_{18}$alkyl are in addition typically heptyl, octyl, 2-ethylhexyl, nonyl, decyl, dodecyl, tetradecyl, hexadecyl or octadecyl.

C$_1$–C$_{18}$Alkoxy, also in C$_1$–C$_{18}$alkoxycarbonyl, is typically methoxy, ethoxy, n-propoxy, isopropoxy, butoxy, hexyloxy, decyloxy, dodecyloxy, hexadecyloxy or octadecyloxy.

C$_1$–C$_{18}$Alkylmercapto is, for example, methylmercapto, ethylmercapto, propylmercapto, butylmercapto, octylmercapto, decylmercapto, hexadecylmercapto or octadecylmercapto.

$C_1$–$C_{18}$Alkylamino is, also in $C_1$–$C_{18}$alkylaminocarbonyl, typically methylamino, ethylamino, propylamino, hexylamino, decylamino, hexadecylamino or octadecylamino.

$C_5$–$C_6$Cycloalkyl is typically cyclopentyl and cyclohexyl.

Important radicals containing the residue of an active methylene, Y, include radicals derivable from various acetoacetanilides, cyanoacetanilides and benzoylacetanilides, such as ethylacetoacetate, ethyl malonate, ethyl cyanoacetate, ethyl benzoyl acetate and malononitrile.

Important radicals of the formula X—C(=O)—O— include esters derivable from a $C_1$–$C_{24}$-aliphatic acids, such as acetic acid, stearic acid, oleic acid, linoleic acid, acrylic acid, methacrylic acid or trifluoroacetic acid, a $C_6$–$C_{24}$araliphatic acid, such as benzoic acid, phenyl acetic acid, phenyl propionic acid or indole acetic acid, a resin acid, such as abeitic acid, behemic acid, a naphthenic acid, a dimeric acid, wherein the aliphatic acids and araliphatic acids are unsubstituted or substituted by one or more customary substituents.

Important radicals of the formula X—C(=O)NR$_{10}$— and X—SO$_2$—NR$_{10}$— include those derivable from amides and sulfonamides prepared from an aliphatic amine and an aliphatic carboxylic or sulfonic acid, an aromatic amine and a aliphatic carboxylic or sulfonic acid, or an aromatic amine and an aromatic or araliphatic carboxylic or sulfonic acid. Suitable radicals of the formula X—C(=O)NR$_{10}$— and X—SO$_2$—NR$_{10}$ especially include those wherein X is $C_1$–$C_{24}$ alkyl, phenyl, benzyl, tolyl, naphthyl and R$_{10}$ is hydrogen, methyl, ethyl, n-propyl, isopropyl, phenyl, benzyl.

Important radicals of the formulae X—SO$_2$—, X—SO$_2$—O— and X—C(=S)—O— include those wherein X is a $C_1$–$C_{24}$ aliphatic radical, an $C_6$–$C_{18}$ aromatic radical, a $C_1$–$C_{24}$ araliphatic radical, a 5, 6 or 7 membered heterocyclic ring, or a fused ring system containing a 5, 6 or 7 membered heterocyclic ring, such as pentyl, hexyl, phenyl, benzyl, tolyl, naphthyl, pyridinyl or indolyl. Important radicals of the formula X—SO$_2$—O— include those derivable from p-toluene sulfonic acid, naphthalene sulfonic acid, pentane sulfonic acid or a water-soluble dye which contains a —SO$_3$H water-solublizing group.

Important radicals of the formula XZN— include those derivable from N,N-di $C_1$–$C_{24}$-alkylamines, such as dimethylamine, diethylamine dipropylamine, and dibutylamine, arylamines, such as N,N-diphenylamine, aralkylamines, such as N,N-dibenzylamine or ethylphenylamine, or heteroaryl amines, such as aminopyridine. The formula XZN— also includes those radicals wherein X and Z, together, along with the nitrogen atom, form a 3 to 8 membered ring, especially a 5 or 6 membered ring, such as a piperazine, morpholine, thiomorpholine, pyrrolidine or piperidine ring.

Important radicals of the formulae XO— include those wherein X is a $C_1$–$C_{24}$ aliphatic radical, a $C_5$–$C_{10}$ alicyclic radical, phenyl, benzyl, naphthyl, or a radical H—(CH$_2$CHR$_{11}$O)$_m$—CH$_2$CHR$_{11}$—, wherein R$_{11}$ is hydrogen or methyl, especially hydrogen, and m is a number from 1 to 20.

Important radicals of the formula XS— include those wherein X is a $C_1$–$C_{24}$ aliphatic radical, a $C_5$–$C_{10}$ alicyclic radical, phenyl, benzyl and naphthyl.

Important radicals of the formula

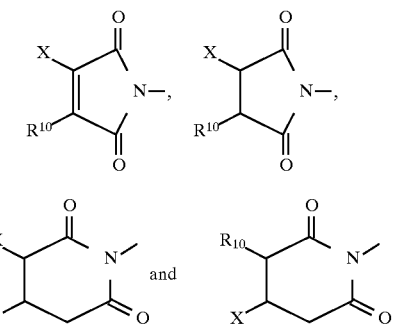

include radicals derivable from succinimide, glutarimide, phthalimide, naphthalimide and isoquinoline-1,3-dione.

Important radicals of the formula —N(R$_{10}$)—C(=O)—O—X include those wherein R$_{10}$ is hydrogen, $C_1$–$C_6$alkyl, phenyl or benzyl, especially hydrogen and $C_1$–$C_6$alkyl, and X is $C_1$–$C_6$alkyl, for example, urethane.

Aromatic and heteroaromatic radicals derivable from known dyes, such as azo, azomethine, or fiber-reactive dyes, for example triazine dyes, or known organic pigments, such as diketopyrrolopyrrole, quinacridone, phthalocyanine, indanthrone, isoindoline, isoindolone, flavanthrone, pyranthrone, anthraquinone, thioindigo, perylene and dioxazine pigments are suitable radicals for B$_1$ and B$_2$. Quinacridinyl (derived from a quinacridone) and 1,4-diketo-3,6-diarylpyrrolo[3,4-c]pyrrolyl (derived from a 1,4-diketo-3,6-diarylpyrrolo[3,4-c]pyrrole) radicals are especially suitable radicals for B$_1$ and B$_2$.

Thus, an aspect of the present invention relates to a process of preparing diketopyrrolopyrrole derivatives of the formula (I) wherein B$_1$ and B$_2$ are each a pigment moiety, in particular, a diketopyrrolopyrrole, quinacridone, phthalocyanine, indanthrone, isoindoline, isoindolone, flavanthrone, pyranthrone, anthraquinone, thioindigo, perylene and dioxazine pigment moiety.

1,4-diketo-3,6-diarylpyrrolo[3,4-c]pyrrolyl radicals are especially suitable radicals for B$_1$ and B$_2$. Such radicals are derivable from compounds of the formula

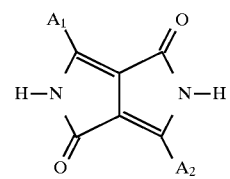

which are well-known as pigments.

When B$_1$ and B$_2$ are 1,4-diketo-3,6-diarylpyrrolo[3,4-c]pyrrolyl radicals, the preferences described above for A$_1$ and A$_2$ apply.

Another aspect of this invention relates to a process for preparing diketopyrrolopyrrole derivatives of formula (I) wherein B$_1$ and B$_2$ are quinacridinyl radicals. Such radicals are derivable from the compounds of the formula

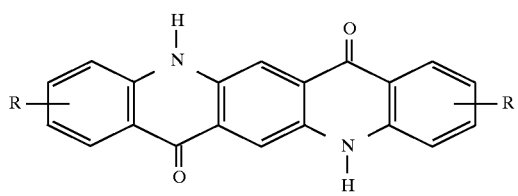

wherein each R is independently hydrogen, halogen, carboxyl, unsubstituted $C_1$–$C_6$-alkyl, $C_1$–$C_6$alkyl which is substituted by halogen, unsubstituted $C_1$–$C_6$alkoxy, or $C_1$–$C_6$alkoxy which is substituted by halogen.

B1 and B2 are especially radicals derivable from quinacridone, 2,9-dichloroquinacridone, 4,11-dichloroqinacridone, 2,9-dimethylquinacridone, 4,11-dimethylquinacridone or 2,9-difluoroquinacridone.

The present invention also relates to a compound of the formula

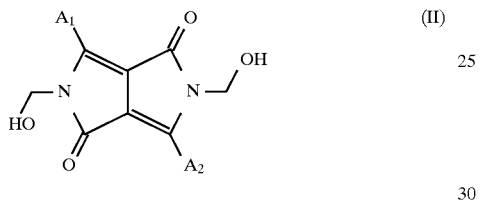

which contains from 0 to 6 moles of —$SO_3M$ per mole of the compound, wherein $A_1$ and $A_2$ are identical or different aryl radicals and M is hydrogen or a metal or ammonium cation.

$A_1$ and $A_2$ have the meanings given above.

Preferably $A_1$ and $A_2$ are radicals of the formula

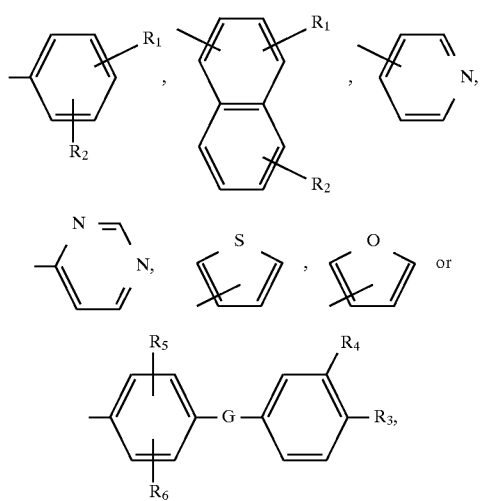

wherein $R_1$ and $R_2$ are each independently of the other hydrogen, halogen, $C_1$–$C_{18}$alkyl, $C_1$–$C_{18}$alkoxy, $C_1$–$C_{18}$alkylmercapto, $C_1$–$C_{18}$alkylamino, $C_1$–$C_{18}$alkoxycarbonyl, $C_1$–$C_{18}$alkylaminocarbonyl, —CN, —$NO_2$, trifluoromethyl, $C_5$–$C_6$cycloalkyl, —C=N—($C_1$–$C_{18}$alkyl), phenyl,

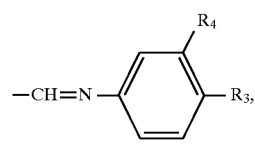

imidazolyl, pyrrazolyl, triazolyl, piperazinyl, pyrrolyl, oxazolyl, benzoxazolyl, benzothiazolyl, benzimidazolyl, morpholinyl, piperidinyl or pyrrolidinyl, G is —$CH_2$—, —CH($CH_3$)—, —C($CH_3$)$_2$—, —CH=N—, —N=N—, —O—, —S—, —SO—, —$SO_2$—, —CONH— or —$NR_7$—, $R_3$ and $R_4$ are each independently of the other hydrogen, halogen, $C_1$–$C_6$alkyl, $C_1$–$C_{18}$alkoxy or —CN, $R_5$ and $R_6$ are each independently of the other hydrogen, halogen or $C_1$–$C_6$alkyl, and $R_7$ is hydrogen or $C_1$–$C_6$alkyl.

In particular, $A_1$ and $A_2$ are radicals of the formula

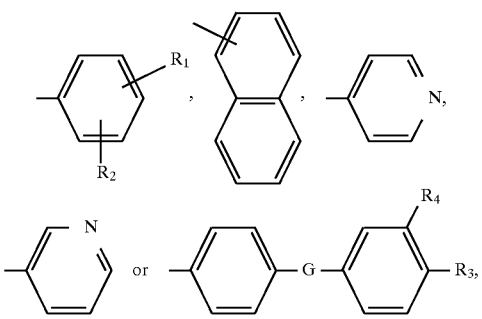

wherein $R_1$ and $R_2$ are each independently of the other hydrogen, chloro, bromo, $C_1$–$C_4$alkyl, $C_1$–$C_6$alkoxy, $C_1$–$C_6$alkylamino, phenyl or CN, G is —O—, —$NR_7$—, —N=N— or —$SO_2$—, $R_3$ and $R_4$ are hydrogen, and $R_7$ is hydrogen, methyl or ethyl.

Most preferably, $A_1$ and $A_2$ are radicals of the formula

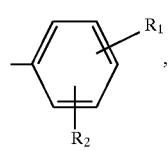

wherein $R_1$ and $R_2$ are each independently of the other hydrogen, methyl, tert-butyl, chloro, bromo, phenyl or CN. Preferably, at least one of $R_1$ and $R_2$ is hydrogen.

Preferably the compounds of formula (II) have from 0 to 4 moles of —$SO_3M$, most preferably from 0 to 2 moles of —$SO_3M$.

The present invention further relates to a process for preparing a compound of the formula

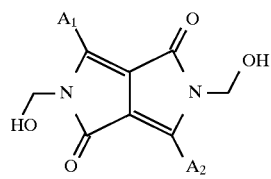

which contains from 0 to 6 moles of —SO$_3$M per mole of the compound, wherein A$_1$ and A$_2$ are identical or different aryl radicals and M is hydrogen or a metal or ammonium cation, which process comprises reacting a 1,4-diketo-3,6-diarylpyrrolopyrrole of the formula

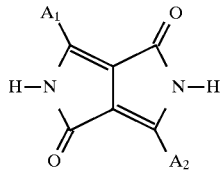

with formaldehyde or paraformaldehyde.

The preferences discussed above relating to the first step of the process for preparing the compounds of formula (I) are applicable to this aspect of the invention.

In particular, the present invention relates to the process wherein the 1,4-diketo-3,6-diarylpyrrolopyrrole is combined with paraformaldehyde in concentrated sulfuric acid; especially wherein the 1,4-diketo-3,6-diarylpyrrolopyrrole and formaldehyde are present in a molar ratio of about 0.75:2 to 1.25:2, most preferably of about 1:2.

If less sulfonation is desired, the reaction is carried out at a temperature of 40° C. or below. The reaction generally proceeds at higher temperatures, for example, in the range from about 20° to 120° C., but higher temperatures generally lead to a higher degree of sulfonation; which may be desirable depending on the intended use of the final product.

The hydroxymethyl derivative of formula (II) is generally isolated by precipitation and filtration, for example by drowning in an organic solvent or water followed by filtration.

In addition to being useful as an intermediate to prepare the diketopyrrolopyrrole derivatives of formula (I), the hydroxymethyl pyrrolopyrrole compound of formula (II) is useful as a stabilizer for polymers.

The diketopyrrolopyrrole derivatives of formula (I) are useful as colorants, such as pigments and dyes, for a variety of materials, in particular paints, plastics and inks, and as additives which influence the rheology characteristics of a pigment composition.

In general, diketopyrrolopyrrole derivatives of formula (I) with a lower degree of sulfonation are most suitable as pigments, while those with a higher degree of sulfonation are useful as dyes and additives.

The following examples further illustrate the preferred embodiments of this invention. In these examples, all parts given are by weight unless otherwise noted.

Example 1

500 grams of concentrated sulfuric acid (95.28%) are added to a one liter four-necked flask equipped with a stirrer, a thermometer and a reflux condenser with a drying tube. 6.2 grams (0.206 moles) of paraformaldehyde are then introduced into the sulfuric acid followed by 28.8 grams (0.1 moles) of 1,4-diketo-3,6-diphenylpyrrolo[3,4-c]pyrrole (unsubstituted DPP) in small portions maintaining the pot temperature below 30° C. The reaction mixture is stirred at 25°±2° C. for 2.5 hours and then poured into ice water, filtered, washed with water until the filtrate is acid free, dried and pulverized to yield 2,5-di(hydroxymethyl)-3,6-diphenylpyrrolo[3,4-c]pyrrole-1,4-dione (analysis C$_{20}$H$_{16}$N$_2$O$_4$).

Examples 2–5

The bis(hydroxymethyl) DPP compounds disclosed in Table 1 are prepared by substituting the appropriate substituted DPP for unsubstituted DPP in the process of Example 1:

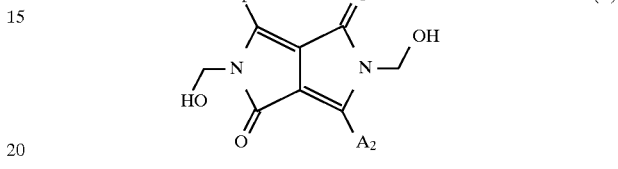

TABLE 1

Bishydroxymethyl DPP derivatives

| A1 | A2 | Mol. Form | Mol. Wt | crystallized from |
|---|---|---|---|---|
| 4-Cl-phenyl | 4-Cl-phenyl | C$_{20}$H$_{14}$Cl$_2$N$_2$O$_4$ | 417 | DMF-MeOH |
| p-tolyl | p-tolyl | C$_{22}$H$_{20}$N$_2$O$_4$ | 376 | DMF-MeOH |
| 4-t-butyl-phenyl | 4-t-butyl-phenyl | C$_{28}$H$_{32}$N$_2$O$_4$ | 460 | DMF-MeOH |
| biphenyl-1-yl | biphenyl-1-yl | C$_{32}$H$_{24}$N$_2$O$_4$ | 500 | DMF-MeOH |

Example 6

250 grams of concentrated sulfuric acid (96%) are added to a one liter four-necked flask equipped with a stirrer, a thermometer and a reflux condenser with a drying tube. 14.4 grams (0.05 moles) of 1,4-diketo-3,6-diphenylpyrrolo[3,4-c]pyrrole (unsubstituted DPP) are added in small portions maintaining the pot temperature below 25° C. 3.1 grams (0.103 moles) of paraformaldehyde are then introduced into the reaction mixture. The reaction mixture is stirred at 25°±2° C. for four hours and then poured into ice water, filtered, washed with water until the filtrate is acid free, dried and pulverized to yield 2,5-di(hydroxymethyl)-3,6-diphenylpyrrolo[3,4-c]pyrrole-1,4-dione (analysis C$_{20}$H$_{16}$N$_2$O$_4$).

Example 7

401.2 grams of concentrated sulfuric acid (96%) are added to a one liter four-necked flask equipped with a stirrer, a thermometer and a reflux condenser with a drying tube. 17.85 grams (0.05 moles) of 1,4-diketo-3,6-di(4-chlorophenyl)pyrrolo[3,4-c]pyrrole (dichloro DPP) are added in small portions maintaining the pot temperature below 30° C. 3.1 grams (0.103 moles) of paraformaldehyde are then introduced into the reaction mixture. The reaction mixture is stirred at 25°±2° C. for four hours and then poured into ice water, filtered, washed with water until the filtrate is acid free, dried and pulverized to yield 2,5-di(hydroxymethyl)-3,6-di(4-chlorophenyl)pyrrolo[3,4-c]pyrrole-1,4-dione (analysis C$_{20}$H$_{14}$Cl$_2$N$_2$O$_4$).

Example 8

422.9 grams of concentrated sulfuric acid (96%) are added to a one liter four-necked flask equipped with a stirrer, a thermometer and a reflux condenser with a drying tube. 22.0 grams (0.05 moles) of 1,4-diketo-3,6-di(biphenyl-1-yl)pyrrolo[3,4-c]pyrrole (biphenylyl DPP) are added in small portions maintaining the pot temperature below 30° C. 3.1 grams (0.103 moles) of paraformaldehyde are then introduced into the reaction mixture. The reaction mixture is stirred at 25°±2° C. for four hours and then poured into ice water, filtered, washed with water until the filtrate is acid free, dried and pulverized to yield 2,5-di(hydroxymethyl)-3,6-di(biphenyl-1-yl)pyrrolo[3,4-c]pyrrole-1,4-dione (analysis $C_{32}H_{24}N_2O_4$).

Example 9

250 grams of concentrated sulfuric acid (96%) are added to a one liter four-necked flask equipped with a stirrer, a thermometer and a reflux condenser with a drying tube. Quinacridone (31.2 grams, 0.1 moles) is added in small portions followed by 14.4 grams (0.05 moles) of 1,4-diketo-3,6-diphenylpyrrolo[3,4-c]pyrrole (unsubstituted DPP) maintaining the pot temperature between 40°–45° C. After stirring for 0.5 hours, 3.1 grams (0.103 moles) of paraformaldehyde are then introduced into the reaction mixture and the temperature rises to about 50° C. The reaction is stirred at 45°±3° C. for 1 hour and then poured into ice water, filtered, washed with water until the filtrate is acid free, dried and pulverized to yield the compound of the formula

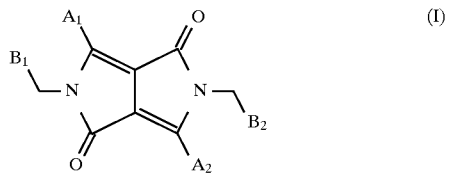

wherein $B_1$ and $B_2$ are quinacridinyl radicals. The product analyzes $C_{60}H_{35.5}N_6O_6 \cdot (SO_3H)_{0.5}$.

Example 10

250 grams of concentrated sulfuric acid (96%) are added to a one liter four-necked flask equipped with a stirrer, a thermometer and a reflux condenser with a drying tube. 14.4 grams (0.05 moles) of 1,4-diketo-3,6-diphenylpyrrolo[3,4-c]pyrrole (unsubstituted DPP) are then added in small portions maintaining the pot temperature below 40° C. After stirring for 0.5 hours, 3.1 grams (0.103 moles) of paraformaldehyde are then introduced into the reaction mixture and the temperature rises to about 45° C. The reaction is stirred at 40°±2° C. for 1 hour. 31.2 grams of quinacridone (0.1 moles) of quinacridone is then added maintaining the temperature below 45° C. The reaction mixture is stirred at 45°±2° C. for 3 hours and then poured into ice water, filtered, washed with water until the filtrate is acid free, dried and pulverized to yield the compound of the formula

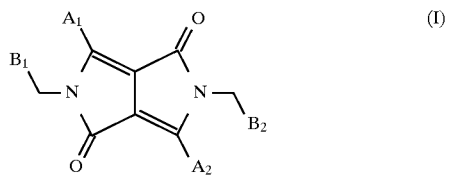

wherein $B_1$ and $B_2$ are quinacridinyl radicals. The product analyzes $C_{60}H_{35.5}N_6O_6 \cdot (SO_3H)_{0.5}$.

Example 11

250 grams of concentrated sulfuric acid (96%) are added to a one liter four-necked flask equipped with a stirrer, a thermometer and a reflux condenser with a drying tube. 14.4 grams (0.05 moles) of 1,4-diketo-3,6-diphenylpyrrolo[3,4-c]pyrrole (unsubstituted DPP) are then added in small portions maintaining the pot temperature below 25° C. After stirring for 1 hour, 3.1 grams (0.103 moles) of paraformaldehyde are then introduced into the reaction mixture followed by 31.2 grams of quinacridone (0.1 moles) and the maintaining the temperature below 25° C. The reaction mixture is stirred at 25°±2° C. for 3 hours and then poured into ice water, filtered, washed with water until the filtrate is acid free, dried and pulverized to yield the compound of the formula

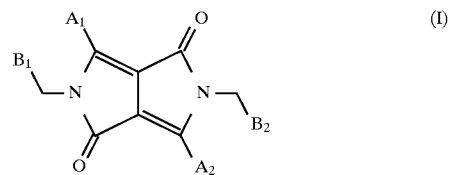

wherein $B_1$ and $B_2$ are quinacridinyl radicals. The product analyzes $C_{60}H_{36}N_6O_6$.

Example 12

400 grams of concentrated sulfuric acid (96%) are added to a one liter four-necked flask equipped with a stirrer, a thermometer and a reflux condenser with a drying tube. 14.4 grams (0.05 moles) of 1,4-diketo-3,6-diphenylpyrrolo[3,4-c]pyrrole (unsubstituted DPP) are then added in small portions maintaining the pot temperature below 25° C. After stirring for 1 hour, 3.1 grams (0.103 moles) of paraformaldehyde are then introduced into the reaction mixture followed by 38.1 grams of 4,11-dichloroquinacridone (0.1 moles) and the maintaining the temperature below 45° C. The reaction mixture is stirred at 45°±2° C. for 2.5 hours and then poured into ice water, filtered, washed with water until the filtrate is acid free, dried and pulverized to yield the compound of the formula

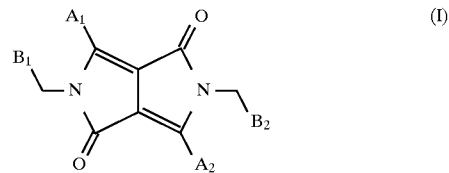

wherein $B_1$ and $B_2$ are 4,11-dichloroquinacridinyl radicals. The product analyzes $C_{60}H_{34}C_{12}N_6O_6$.

Example 13

500 grams of concentrated sulfuric acid (90%) are added to a one liter four-necked flask equipped with a stirrer, a thermometer and a reflux condenser with a drying tube. 6.2 grams (0.206 moles) of paraformaldehyde are then introduced into the sulfuric acid followed by 28.8 grams (0.1 moles) of 1,4-diketo-3,6-diphenylpyrrolo[3,4-c]pyrrole (unsubstituted DPP) in small portions maintaining the pot temperature below 30° C. The reaction mixture is stirred at 25°±2° C. for 2.5 hours and then poured into ice water, filtered, washed with water until the filtrate is acid free, dried and pulverized to yield a mixture of 2,5-di(hydroxymethyl)-3,6-diphenylpyrrolo[3,4-c]pyrrole-1,4-dione and the starting materials. When 85% $H_2SO_4$ replaces the 90% $H_2SO_4$, a mixture containing a major portion of the starting materials is obtained.

Example 14

250 grams of concentrated sulfuric acid (96%) and paraformaldehyde (3.3 g.; 0.11 moles) are added to a one liter four necked flask, equipped with a stirrer, a thermometer, a reflux condenser with a drying tube. Unsubstituted DPP(14.4 g.; 0.05 moles) are added to the sulfuric acid/paraformaldehyde mixture in small portions maintaining the pot temperature between 25°–30° C. This mixture is stirred for 1 hour to ensure complete solution. An additional 200 g of sulfuric acid is then added to the reaction mixture followed by unsubstituted DPP (28.8 g.; 0.1 moles) in small portions, maintaining the pot temperature at 32°–34° C. This reaction mixture is then stirred at 30°±3° C. for 4 hrs and poured into ice-water, filtered, washed with water until the filtrate is acid free, dried and pulverized.

The compound isolated analyzed for $C_{56}H_{36}N_6O_6$ and is believed to have the formula

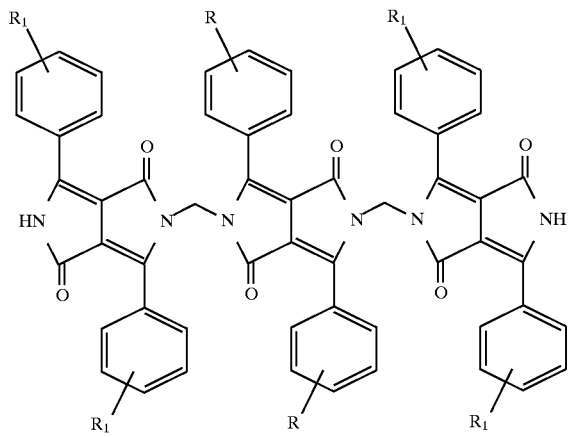

wherein each R and $R_1$ substituent is hydrogen.

The compounds in Table 2 are made by substituting the appropriate pyrrolopyrrole reactants in the process of Example 14.

TABLE 2

DPP-CH$_2$-DPP-CH$_2$-DPP derivatives

| R | $R_1$ | Mol. Form | crystallized from |
|---|---|---|---|
| H | H | $C_{56}H_{36}N_6O_6$ | $H_2SO_4$ |
| H | Cl | $C_{56}H_{32}Cl_4N_6O_6$ | $H_2SO_4$ |
| H | $CH_3$ | $C_{60}H_{44}N_6O_6$ | $H_2SO_4$ |
| H | t-Butyl | $C_{72}H_{68}N_6O_6$ | $H_2SO_4$ |
| H | 4-Phenyl | $C_{80}H_{52}N_6O_6$ | $H_2SO_4$ |
| Cl | H | $C_{56}H_{34}Cl_2N_{O6}$ | $H_2SO_4$ |
| Cl | Cl | $C_{56}H_{30}Cl_6N_6O_6$ | $H_2SO_4$ |
| Cl | $CH_3$ | $C_{60}H_{42}Cl_2N_6O_6$ | $H_2SO_4$ |
| Cl | t-Butyl | $C_{72}H_{66}Cl_2N_6O_6$ | $H_2SO_4$ |
| Cl | 4-Phenyl | $C_{80}H_{50}Cl_2N_6O_6$ | $H_2SO_4$ |
| $CH_3$ | H | $C_{58}H_{40}N_6O_6$ | $H_2SO_4$ |
| $CH_3$ | Cl | $C_{58}H_{36}Cl_4N_6O_6$ | $H_2SO_4$ |
| $CH_3$ | $CH_3$ | $C_{62}H_{48}N_8O_6$ | $H_2SO_4$ |
| $CH_3$ | t-Butyl | $C_{74}H_{72}N_6O_6$ | $H_2SO_4$ |
| $CH_3$ | 4-Phenyl | $C_{82}H_{56}N_6O_6$ | $H_2SO_4$ |
| t-Butyl | H | $C_{64}H_{52}N_6O_6$ | $H_2SO_4$ |
| t-Butyl | Cl | $C_{64}H_{48}Cl_4N_6O_6$ | $H_2SO_4$ |
| t-Butyl | $CH_3$ | $C_{68}H_{60}N_6O_6$ | $H_2SO_4$ |
| t-Butyl | t-Butyl | $C_{80}H_{84}N_6O_6$ | $H_2SO_4$ |
| t-Butyl | 4-Phenyl | $C_{88}H_{68}N_6O_6$ | $H_2SO_4$ |
| 4-Phenyl | H | $C_{68}H_{44}N_6O_6$ | $H_2SO_4$ |
| 4-Phenyl | Cl | $C_{68}H_{40}Cl_4N_6O_6$ | $H_2SO_4$ |
| 4-Phenyl | $CH_3$ | $C_{72}H_{52}N_6O_6$ | $H_2SO_4$ |
| 4-Phenyl | t-Butyl | $C_{84}H_{76}N_6O_6$ | $H_2SO_4$ |
| 4-Phenyl | 4-Phenyl | $C_{92}H_{60}N_6O_6$ | $H_2SO_4$ |

Example 15

250 grams of concentrated sulfuric acid (96%) and paraformaldehyde (3.3 g.; 0.11 moles) are added to a one liter four necked flask, equipped with a stirrer, a thermometer, a reflux condenser with a drying tube. Unsubstituted DPP(14.4 g.; 0.05 moles) are added to the sulfuric acid/paraformaldehyde mixture in small portions maintaining the pot temperature between 30°–35° C. This mixture is stirred for 1 hour to ensure complete solution. An additional 200 g of sulfuric acid is then added to the reaction mixture followed by unsubstituted DPP(28.8 g.; 0.1 moles) in small portions, maintaining the pot temperature at 38°–42° C. This reaction mixture is then stirred at 40°±3° C. for 4 hrs and poured into ice-water, filtered, washed with water until the filtrate is acid free, dried and pulverized.

The compound isolated analyzed for $C_{56}H_{36}N_6O_6 \cdot (SO_3H)_{0.5}$

The sulfonated derivatives of the compounds of Table 2 are prepared by substituting the appropriate pyrrolopyrrole reactants in the process of Example 15.

Example 16

Bishydroxymethyl DPP (17.4 g, 0.05 moles), aniline (9.3 g, 0.1 moles) and DMF (100 ml) are added to a one liter four necked flask, equipped with a stirrer, a thermometer, and a reflux condenser with a drying tube. The mixture is stirred at 100° C. for 4 hrs, then diluted with water, filtered, washed with water, dried and pulverized to give 2,5-di-(anilinomethyl)-3,6-diphenyl pyrrolo[3,4-c]pyrrole-1,4-dione (bisanilinomethyl DPP).

Example 17

Bishydroxymethyl DPP (17.4 g, 0.05 moles), a catalytic amount of paratoluene sulfonic acid and methanol (100 ml) are added to a one liter four necked flask, equipped with a stirrer, a thermometer, and a reflux condenser with a drying tube. The mixture is stirred at reflux for 4 hrs., diluted with water, filtered, washed with water, dried and pulverized to give 2,5-di(methoxymethyl)-3,6-diphenyl pyrrolo[3,4-c]pyrrole-1,4-dione (bismethoxymethyl DPP).

Example 18

Bishydroxymethyl-di-t-butyl DPP (23.0 g, 0.05 moles), a catalytic amount of paratoluene sulfonic acid and methanol (100 ml) are added to a one liter four necked flask, equipped with a stirrer, a thermometer, and a reflux condenser with a drying tube. The mixture is stirred at reflux for 4 hrs, diluted with water, filtered, washed with water, dried and pulverized to give 2,5-di(methoxymethyl)-3,6-di-t-butylphenyl pyrrolo[3,4-c]pyrrole-1,4-dione (bismethoxymethyl di-t-butyl DPP).

I claim:

1. A process for the preparation of a diketopyrrolopyrrole compound of the formula (I)

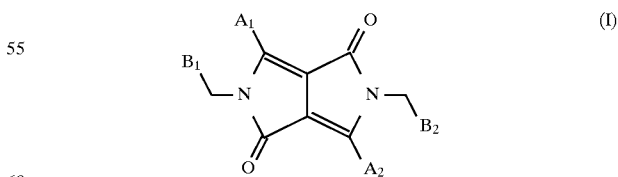

(I)

wherein $A_1$ and $A_2$ are identical or different aryl radicals and $B_1$ and $B_2$ are identical or different organic radicals; which diketopyrrolopyrrole compound has from 0 to 6 moles of —$SO_3M$ per mole of diketopyrrolopyrrole compound; wherein M is hydrogen or a metal or ammonium cation, which process comprises a reaction wherein a 1,4-diketo-3,6-diarylpyrrolopyrrole of the formula

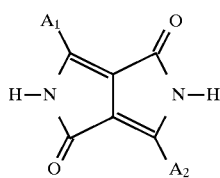

is reacted in a first step with formaldehyde to yield a sulfonated or non-sulfonated intermediate of the formula

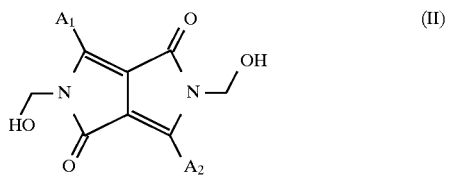

which reacts in a second step with a precursor of the organic radicals, $B_1$ and $B_2$, to yield the diketopyrrolopyrrole compound of formula (I).

2. A process of claim 1 wherein the precursor reacts with the hydroxy groups of the intermediate of formula (II) by a substitution reaction or to form an —O— linkage.

3. A process of claim 1 wherein the first step is carried out by combining the 1,4-diketo-3,6-diarylpyrrolopyrrole with formaldehyde or paraformaldehyde in concentrated sulfuric acid.

4. A process of claim 3 wherein the 1,4-diketo-3,6-diarylpyrrolopyrrole and formaldehyde are present in a molar ratio of about 1:2.

5. A process of claim 3 wherein the process is carried out at a temperature of 40° C. or below.

6. A process of claim 1 wherein the second step is carried out without isolating the intermediate of formula (II).

7. A process of claim 1 wherein the intermediate of formula (II) is isolated prior to carrying out the second step.

8. A process of claim 5 wherein the diketopyrrolopyrrole compound of formula (I) contains from 0 to 2 moles of —$SO_3M$ per mole of diketopyrrolopyrrole compound.

9. A process of claim 1 wherein the precursor of the organic radicals, $B_1$ and $B_2$, is a 1,4-diketo-3,6-diarylpyrrolo[3,4-c]pyrrole or a quinacridone.

* * * * *